US010039618B2

(12) United States Patent
Nazeck

(10) Patent No.: US 10,039,618 B2
(45) Date of Patent: Aug. 7, 2018

(54) ORTHODONTIC BRACKETS

(71) Applicant: Ormco Corporation, Orange, CA (US)

(72) Inventor: Benjamin Mark Nazeck, San Dimas, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 15/251,241

(22) Filed: Aug. 30, 2016

(65) Prior Publication Data

US 2017/0065376 A1 Mar. 9, 2017

Related U.S. Application Data

(60) Provisional application No. 62/214,555, filed on Sep. 4, 2015.

(51) Int. Cl.
*A61C 3/00* (2006.01)
*A61C 7/28* (2006.01)

(52) U.S. Cl.
CPC .................... *A61C 7/287* (2013.01)

(58) Field of Classification Search
CPC .... A61C 7/12; A61C 7/14; A61C 7/28; A61C 7/287
USPC ....................................... 433/8, 10
See application file for complete search history.

(56) References Cited

U.S. PATENT DOCUMENTS

| 812,328 | A | | 2/1906 | Crenshaw | |
|---|---|---|---|---|---|
| 3,964,165 | A | | 6/1976 | Stahl et al. | |
| 4,681,538 | A | * | 7/1987 | DeLuca | A61C 7/14 433/9 |
| 4,799,882 | A | | 1/1989 | Kesling | |
| 4,819,316 | A | | 4/1989 | Rossini et al. | |
| 5,299,934 | A | * | 4/1994 | Suyama | A61C 7/12 433/10 |
| 5,466,151 | A | | 11/1995 | Damon | |
| 7,704,072 | B2 | * | 4/2010 | Damon | A61C 7/287 433/11 |

(Continued)

FOREIGN PATENT DOCUMENTS

| EP | 0381520 A1 | 8/1990 |
|---|---|---|
| EP | 0397533 A2 | 11/1990 |

(Continued)

OTHER PUBLICATIONS

European Patent Office, Search Report and Preliminary Opinion issued in corresponding EP Application No. 16187102 dated Nov 18, 2016, 7 pp.

*Primary Examiner* — Gwen M Demosky
(74) *Attorney, Agent, or Firm* — Wood Herron & Evans LLP

(57) ABSTRACT

An orthodontic bracket for coupling an archwire having a ligature to a tooth includes a bracket body configured to be mounted to the tooth, the bracket body including an archwire slot opened to one side of the bracket body and adapted to receive the archwire therein. At least two tie wings extend from the bracket body, the at least two tie wings each having a tip region and an under tie wing region, and the under tie wing region is configured to receive the ligature. The under tie wing regions each include a curvature in a plane parallel to a longitudinal axis of the archwire slot and extending in the same direction that the archwire slot opens at a location adjacent an outer end of the under tie wing region.

12 Claims, 8 Drawing Sheets

(56) References Cited

U.S. PATENT DOCUMENTS

| | | | | |
|---|---|---|---|---|
| 8,029,276 B1* | 10/2011 | Lokar | ................... | A61C 7/287 |
| | | | | 433/10 |
| 8,033,824 B2 | 10/2011 | Oda et al. | | |
| 2007/0224569 A1* | 9/2007 | Oda | ................... | A61C 7/02 |
| | | | | 433/10 |
| 2008/0020338 A1* | 1/2008 | Zakhem | ................ | A61C 7/143 |
| | | | | 433/9 |
| 2009/0004619 A1* | 1/2009 | Oda | ................... | A61C 7/14 |
| | | | | 433/24 |
| 2010/0055636 A1* | 3/2010 | Yeh | ................... | A61C 7/287 |
| | | | | 433/10 |
| 2011/0287378 A1 | 11/2011 | Dupray et al. | | |
| 2012/0295213 A1 | 11/2012 | Andrews et al. | | |
| 2013/0071803 A1 | 3/2013 | Stevens et al. | | |
| 2013/0280668 A1* | 10/2013 | Upchurch, Jr. | ........ | A61C 7/143 |
| | | | | 433/9 |
| 2013/0309624 A1* | 11/2013 | Smith | ................... | A61C 7/285 |
| | | | | 433/9 |
| 2015/0223914 A1* | 8/2015 | Sabilla | ................. | A61C 7/287 |
| | | | | 433/11 |
| 2015/0272706 A1* | 10/2015 | Tan | ................... | A61C 7/141 |
| | | | | 433/8 |

FOREIGN PATENT DOCUMENTS

| | | |
|---|---|---|
| EP | 0588961 B1 | 2/1999 |
| EP | 1401349 A1 | 3/2004 |
| EP | 1795147 A1 | 6/2007 |
| EP | 1836990 A1 | 9/2007 |
| EP | 2425798 A2 | 3/2012 |
| WO | 2009068145 A2 | 6/2009 |
| WO | 2009141825 A2 | 11/2009 |

* cited by examiner

ORTHODONTIC BRACKETS

TECHNICAL FIELD

The invention relates generally to orthodontic brackets, and more particularly to orthodontic brackets having tie wings.

BACKGROUND

Orthodontic brackets represent a principal component of all corrective orthodontic treatments devoted to improving a patient's occlusion. In conventional orthodontic treatments, a clinician or an assistant affixes brackets to the patient's teeth and then engages an archwire into a slot of each bracket. The archwire applies corrective forces that coerce the teeth to move into correct orthodontic positions. Traditional ligatures, such as small elastomeric O-rings or elastic power chains may be employed to retain the archwire within each bracket slot by way of tie wings.

Self-ligating orthodontic brackets have been developed that eliminate the need for ligatures by relying on a movable member, such as a latch or slide, for retaining the archwire within the bracket slot. However, many self-ligating orthodontic brackets include tie wings and employ ligatures or power chains that secure the archwire within the archwire slot during selected stages of orthodontic treatment. Ligatures or power chains may facilitate coupling of the bracket to other adjacent orthodontic devices.

Traditionally, a ligature or a power chain is manually engaged by the clinician by stretching it over the bracket and the archwire and securing it under the tie wings. The ligature remains in a stretched condition during treatment. During installation, once the ligature or power chain has cleared a corner of the bracket, the elasticity of the ligature or power chain, as a result of it being stretched, pulls it into the area under the tie wing (the "under-tie wing area"), effectively seating the ligature to the orthodontic bracket and securing the archwire to the orthodontic bracket. During this installation process, the ligature or power chain must be elastic enough to clear the corner of the bracket and then retract enough to sufficiently secure the archwire to the orthodontic bracket. In some instances, the large degree of stretching causes ligatures to break during use.

By way of example, ligatures may break when they are stretched during installation onto a bracket. When this occurs, the orthodontist must remove the broken ligature and secure another ligature in its place. In addition, it is not uncommon for ligatures to break after initial installation and during treatment. As such, this type of breakage typically occurs when the patient is not at the clinician's office. As a consequence, the patient may make an unplanned visit to the clinician to replace the broken ligature. During the time between ligature breakage and the office visit, orthodontic treatment may not be as efficient or according to the orthodontist's treatment plan. This may, in turn, increase treatment time and the time the patient must wear the braces.

Therefore, a need exists for orthodontic brackets that reduce the risk of ligature failure and facilitate ligature installation.

SUMMARY

An orthodontic bracket for coupling an archwire having a ligature to a tooth includes a bracket body configured to be mounted to the tooth, the bracket body including an archwire slot opened to one side of the bracket body and adapted to receive the archwire therein. At least two tie wings extend from the bracket body, the at least two tie wings each having a tip region and an under tie wing region, wherein the under tie wing region is configured to receive the ligature. The under tie wing regions each include a curvature in a plane parallel to a longitudinal axis of the archwire slot and extend in the same direction that the archwire slot opens at a location adjacent an outer end of the under tie wing region.

In an exemplary embodiment, the curvature of each under tie wing region may be defined by a radius of at least about 0.010 inch. More particularly, the curvature of each under tie wing region may be defined by a radius of at least 0.030 inch. Additionally, the tip regions of the at least two tie wings may each include a curvature in the same direction as the curvature of the corresponding under tie wing region. In an exemplary embodiment, the curvature of each tip region may be defined by a radius of at least about 0.010 inch. More particularly, the curvature of each tip region may be defined by a radius of at least 0.030 inch. In one embodiment, the curvature of each tip region is substantially the same as the curvature of the corresponding under tie wing region. The under tie wing regions may each be positioned above a base surface of the archwire slot in the same direction that the archwire slot opens at a location adjacent an outer end of the under tie wing region. The orthodontic bracket may further include a linearly extending portion between the under tie wing regions.

Furthermore, each under tie wing region may have a concave curvature in a first plane perpendicular to the longitudinal axis of the archwire slot. Moreover, each tip region may have a convex curvature in the first plane perpendicular to the longitudinal axis of the archwire slot so as to form an S-shaped curve between each under tie wing region and the corresponding tip region in the first plane perpendicular to the longitudinal axis of the archwire slot. In one embodiment, the under tie wing region has a concave curvature in a second plane perpendicular to the longitudinal axis of the archwire slot substantially equal to the corresponding concave curvature in the first plane perpendicular to the longitudinal axis of the archwire slot, such that the concave curvature is substantially constant along at least a portion of the under tie wing region between the first and second planes.

In another embodiment an orthodontic bracket for coupling an archwire having a ligature to a tooth includes a bracket body configured to be mounted to the tooth, the bracket body including an archwire slot opened to one side of the bracket body and adapted to receive the archwire therein. At least two tie wings extend from the bracket body, the at least two tie wings each having a tip region and an under tie wing region, wherein the under tie wing region is configured to receive the ligature. The tip regions each include a radius of curvature in the same direction that the archwire slot opens at a location adjacent an outer end of the corresponding under tie wing region.

In yet another embodiment, an orthodontic bracket for coupling an archwire having a ligature to a tooth includes a bracket body configured to be mounted to the tooth, the bracket body including an archwire slot adapted to receive the archwire therein, a first tie wing extending from an occlusal side of the bracket body adjacent a mesial side of the bracket body, a second tie wing extending from the occlusal side adjacent a distal side of the bracket body, a third tie wing extending from a gingival side of the bracket body adjacent the mesial side, and a fourth tie wing extending from the gingival side adjacent the distal side. An occlusal under tie wing region extends between the first and second tie wings, and a gingival under tie wing region extends between the third and fourth tie wings. The occlusal and gingival under tie wing regions each include at least one labially curved portion which extends in a mesial-distal direction and follows a labially curved path proximate at least one of the mesial or distal sides of the bracket body.

BRIEF DESCRIPTION OF THE DRAWINGS

The accompanying drawings, which are incorporated in and constitute a part of this specification, illustrate embodiments of the invention and, together with a detailed description given below, serve to explain the invention.

DETAILED DESCRIPTION

Ligature breakage is common in orthodontic treatment. The current solution to address this problem is to replace the broken ligature with a new one. The cost and time to do that is minimal, so clinicians simply practice with an expectation that some ligatures will break and the clinician will have to replace them. The term "ligature" is used herein with reference to elastomeric ligatures. These include, but are not limited to, O-ring type ligatures, such as Molded "O"s and Power Chains, both available from Ormco Corporation, Orange Calif. Without being bound by theory, it is thought that ligature breakage, while being inherent in the nature of the elastomeric material, is also related to the orthodontic bracket onto which the ligature is placed. In that regard, a clinician may experience difficulty in stretching a ligature around an orthodontic bracket and archwire without tearing the ligature. The further the ligature has to be stretched to install it, the more it is in tension and is at risk of tearing. It is believed that bracket geometry and the orientation of the archwire slot relative to the tie wings can cause undo tension on and thus result in a tear in the ligature during installation and even during use. As a result, the ligature may fail catastrophically starting at that location.

Poor geometry in the orthodontic bracket may be the result of a desire to manufacture brackets at a reduced cost without realization that cost reduction negatively impacts ligature breakage. For example, twin tie wings are typically machined from a block of stainless steel or the bracket body is made by casting it metallurgically. Applicant has identified that machining and metal casting, while being cost effective, are limited in capability for certain bracket geometries and often create undesirable geometries from the perspective of ligature breakage. In view of the minimal cost and time to replace broken ligatures, orthodontic bracket manufacturers have not yet associated bracket geometry with ligature failure.

More specifically, it is believed that prior bracket designs require the ligature to navigate a sharp, near 90°, transition from under the tie wing up over an archwire seated in the archwire slot. Applicant has identified this as an undesirable geometry that creates a stress riser in the ligature at the point of contact between the ligature and the archwire. This configuration increases the risk of ligature breakage during orthodontic treatment.

Figure 1:
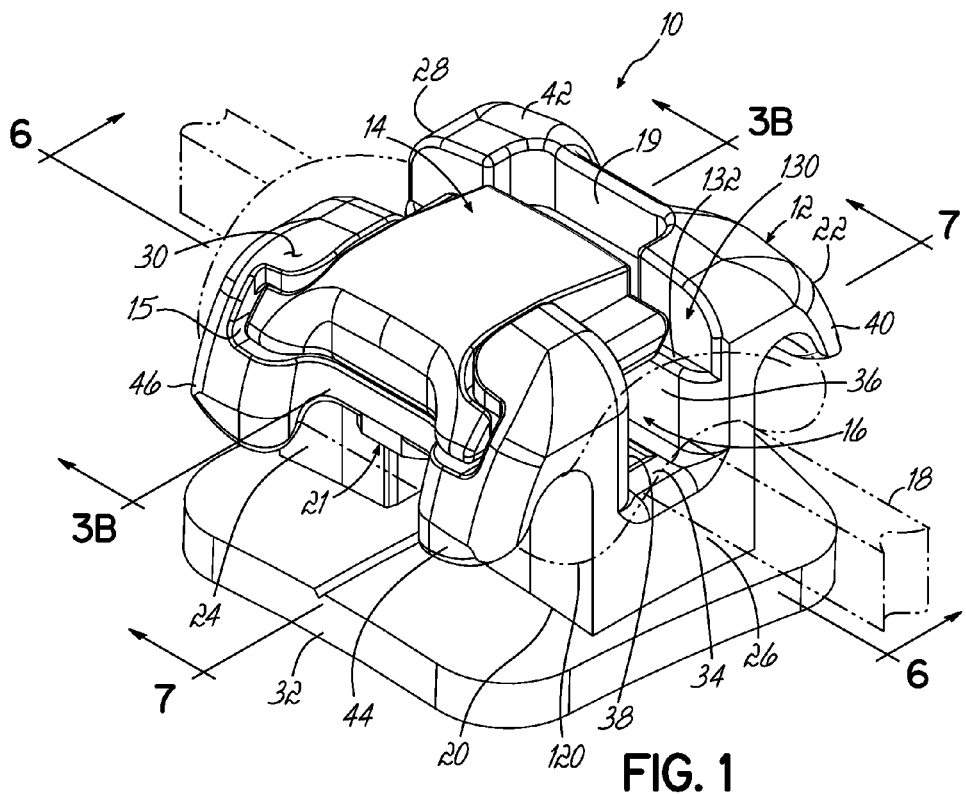
FIG. 1 is a perspective view of an orthodontic bracket in accordance with one embodiment of the invention.
Figure 2:
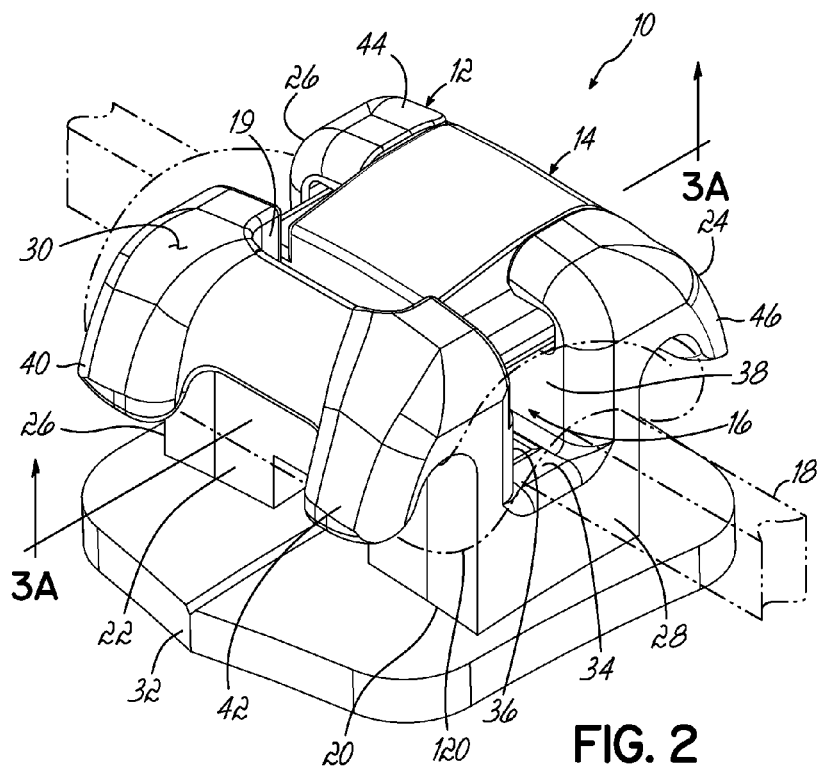
FIG. 2 is an alternative perspective view of the orthodontic bracket of FIG. 1.

To address ligature breakage during installation and during orthodontic treatment, and referring now to FIGS. 1 and 2, according to one embodiment of the present invention, an orthodontic bracket 10 includes a bracket body 12 defining an archwire slot 16 formed therein. The archwire slot 16 is adapted to receive an archwire 18 (shown in phantom) for applying corrective forces to the teeth. The bracket body 12 may include two or more tie wings, described below, which are rounded or curved in one or both of the mesial-distal and occlusal-gingival directions relative to the archwire slot 16 and are located relative to the archwire slot 16 so as to reduce abrupt transitions in the orientation of a ligature 120 when it is installed under the tie wings and over the archwire. The curvatures described herein are more than simply a break in the edges of all these surfaces to form rounded edges.

To those ends, the orthodontic bracket 10 may be a self-ligating orthodontic bracket that includes a movable closure member coupled to the bracket body 12. By way of example only, the movable closure member may be a ligating slide 14 that is slidably coupled with the bracket body 12 via a slide engagement track 15 so as to be slidable between an opened position (not shown) and a closed position (shown in FIGS. 1 and 2) to capture the archwire 18 therein. As shown, a ligature 120 may secure the archwire 18 within the archwire slot 16 during treatment. While a self-ligating orthodontic bracket is shown in the figures and described herein, embodiments of the present invention include twin tie wing type orthodontic brackets and other orthodontic brackets that do not include a movable ligating member. These types of brackets are most often used in conjunction with ligatures, both elastomeric and metallic, to retain an archwire in the archwire slot. Moreover, while the movable closure member is described herein as a ligating slide, the invention is not so limited, as the movable closure member may include other movable structures (e.g., latch, spring clip, door, etc.) that are capable of moving between an opened and closed position.

The orthodontic bracket 10, unless otherwise indicated, is described herein using a reference frame attached to a labial surface of a tooth on the lower jaw. Consequently, as used herein, terms such as labial, lingual, mesial, distal, occlusal, and gingival used to describe orthodontic bracket 10 are relative to the chosen reference frame. The embodiments of the invention, however, are not limited to the chosen reference frame and descriptive terms, as the orthodontic bracket 10 may be used on other teeth and in other orientations within the oral cavity. For example, the orthodontic bracket 10 may also be coupled to the lingual surface of the tooth and be within the scope of the invention. Those of ordinary skill in the art will recognize that the descriptive terms used herein may not directly apply when there is a change in reference frame. Nevertheless, embodiments of the invention are intended to be independent of location and orientation within the oral cavity and the relative terms used to describe embodiments of the orthodontic bracket are to merely provide a clear description of the embodiments in the drawings. As such, the relative terms labial, lingual, mesial, distal, occlusal, and gingival are in no way limiting the invention to a particular location or orientation.

In that regard, in an exemplary orientation, when mounted to the labial surface of a tooth carried on the patient's lower jaw, the bracket body 12 has a lingual side 20, an occlusal side 22, a gingival side 24, a mesial side 26, a distal side 28, and a labial side 30. The lingual side 20 of the bracket body 12 is configured to be secured to the tooth in any conventional manner, for example, by an appropriate orthodontic cement or adhesive or by a band around an adjacent tooth.

The lingual side 20 may further be provided with a pad 32 defining a bonding base that is secured to the surface of the tooth by an adhesive. The pad 32 may be coupled to the bracket body 12 as a separate piece or element or, alternatively, the pad 32 may be integrally formed with the bracket body 12. A coupling element in the form of, for example, an orthodontic hook having a shaft and bulbous end (not shown) may extend from the bracket body 12 and facilitate coupling of the bracket body 12 with other orthodontic elements such as bands or other hooks on adjacent teeth.

Figure 3A:
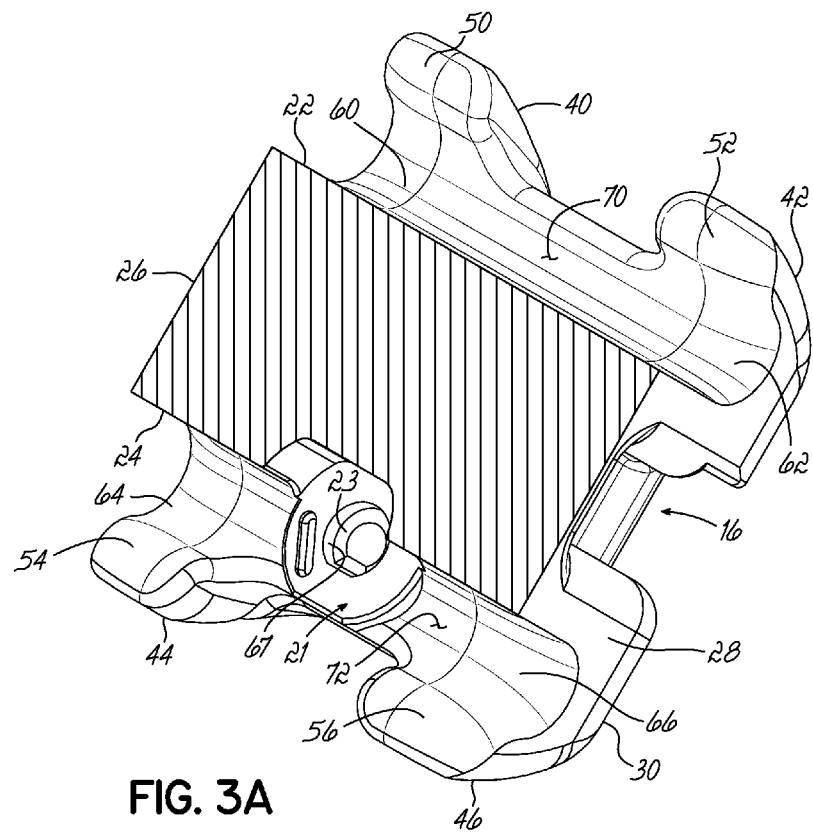
FIG. 3A is a cross-sectional view of the orthodontic bracket of FIG. 2, taken along section line 3A-3A.
Figure 3B:
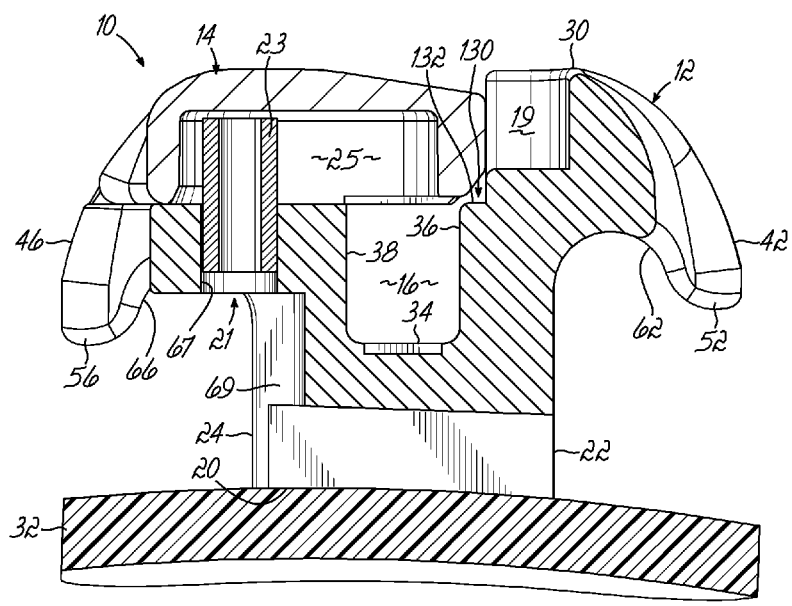
FIG. 3B is a cross-sectional view of the orthodontic bracket of FIG. 1, taken along section line 3B-3B.

With reference to FIGS. 1, 2, and 3B, the bracket body 12 includes a base surface 34 and a pair of opposed slot surfaces 36, 38 projecting labially from the base surface 34 that collectively define the archwire slot 16. Accordingly, the base surface 34 and the opposed slot surfaces 36, 38 extend in a mesial-distal direction from mesial side 26 to distal side 28 of the bracket body 12. The opposed slot surfaces 36, 38 and base surface 34 are substantially encapsulated or embedded within the material of the bracket body 12. The archwire slot 16 of the bracket body 12 may be designed to receive the archwire 18 in any suitable manner.

In one embodiment, the orthodontic bracket 10 may be provided with a securing mechanism 21 (shown best in FIGS. 3A and 3B) such as that described in U.S. Pat. No. 8,033,824, which is incorporated by reference herein in its entirety. The securing mechanism 21 may include a generally elongated, tubular spring pin 23 inserted into a bore 67 in the bracket body 12. The spring pin 23 may cooperate with a retaining slot 25 formed in the ligating slide 14 to guide the ligating slide between the opened and closed positions and may lock the ligating slide in one or both positions during orthodontic treatment. As shown, the spring pin 23 may be accessible via a cutout 69 of the bracket body 12.

Referring to FIGS. 1 and 3B, the bracket body 12 may include a tool receptacle 19 to receive a tool (not shown) that the clinician may use to slide the ligating slide 14 to the opened position from the closed position.

As shown in FIGS. 1 and 2, the bracket body 12 includes tie wings which receive the ligature 120. In the exemplary embodiment, the bracket body 12 includes four tie wings, specifically, first and second tie wings 40, 42 (i.e., occlusal tie wings) that extend from the occlusal side 22 of the bracket body 12, and third and fourth tie wings 44, 46 (i.e., gingival tie wings) that extend from the gingival side 24 of the bracket body 12. In the embodiment shown, the first and third tie wings 40, 44 are adjacent the mesial side 26 of the bracket body 12, and the second and fourth tie wings 42, 46 are adjacent the distal side 28 of the bracket body 12. The tie wings 40, 42, 44, 46 are thus spaced apart and essentially define the four distant-most corners of the bracket body 12. As is known, the tie wings 40, 42, 44, 46 facilitate coupling of the orthodontic bracket 10 to other orthodontic devices, such as the archwire 18, with the ligature 120. While the ligature 120 is shown as being circular, it will be appreciated that other ligature configurations may be utilized according to embodiments of the invention.

As described above, in general, each tie wing 40, 42, 44, 46 is rounded or curved and positioned in a specific manner that reduces stress points on the ligature 120 during its installation on the orthodontic bracket 10 and during orthodontic treatment. Advantageously, ligature breakage during installation and during orthodontic treatment may be reduced. Specifically, and with reference to FIGS. 3A and 4, each of the tie wings 40, 42, 44, 46 includes a respective tip region 50, 52, 54, 56 and a respective under tie wing region 60, 62, 64, 66 each of which may be curved in both the mesial-distal and occlusal-gingival directions, that is, they each may be curved in a plane perpendicular to and in a plane parallel to the longitudinal axis of the archwire slot 16, as is described below.

To that and other ends, in one embodiment, the bracket body 12 includes an occlusal mid-body region 70 that extends mesial-distally along the occlusal side 22 of the bracket body 12 between the first tie wing 40 and the second tie wing 42, and meshes to be continuous with the under tie wing regions 60 and 62 proximate the mesial side 26 and distal side 28, respectively. Similarly, the bracket body 12 includes a gingival mid-body region 72 that extends mesial-distally along the gingival side 24 between the third tie wing 44 and the fourth tie wing 46 and meshes with the under tie wing regions 64 and 66 proximate the mesial side 26 and distal side 28, respectively. While mid-body regions 70, 72 are shown and described, embodiments of the present invention are not limited to those that include mid-body regions between spaced apart tie wings, as shown. For example, orthodontic brackets may include a single tie wing on each side of the archwire slot (i.e., two tie wings, one extending occlusally and the other extending gingivally, as is common with self-ligating orthodontic brackets), and those tie wings may extend substantially from the mesial side to the distal side and thus the mid-body regions 70, 72 would be absent.

As best shown in FIGS. 3A and 3B, the mid-body regions 70 and 72 are curved having a U-shaped cross-section in the occlusal-gingival direction such that they each exhibit a trough-like appearance. The curvature of the mid-body regions 70 and 72 in a plane perpendicular to a longitudinal axis of the archwire slot 16 may correspond to a cross-sectional profile of the ligature, such that the ligature may be supported along a large portion of its circumference when in the mid-body regions 70, 72. For example, the mid-body regions 70 and 72 may have circular cross sections of a diameter substantially equal to or greater than a diameter of the ligature. In one embodiment, the mid-body regions 70 and 72 may define a circular cross section of approximately 0.022 inch in diameter.

With continued reference to FIG. 3A, a bottom surface of the securing mechanism 21 may interrupt the mid-body region 72. However, the bottom surface of the securing mechanism 21 may be configured to minimize interference with the path of a ligature received by the tie wings 44, 46. For example, although not shown, the bottom surface of the securing mechanism 21 may be generally flush with at least a portion of the mid-body region 72. In this way, the bottom surface of the securing mechanism 21 may be considered to form part of the mid-body region 72. Alternatively, the securing mechanism 21 may be recessed from the mid-body region 72.

Figure 5:
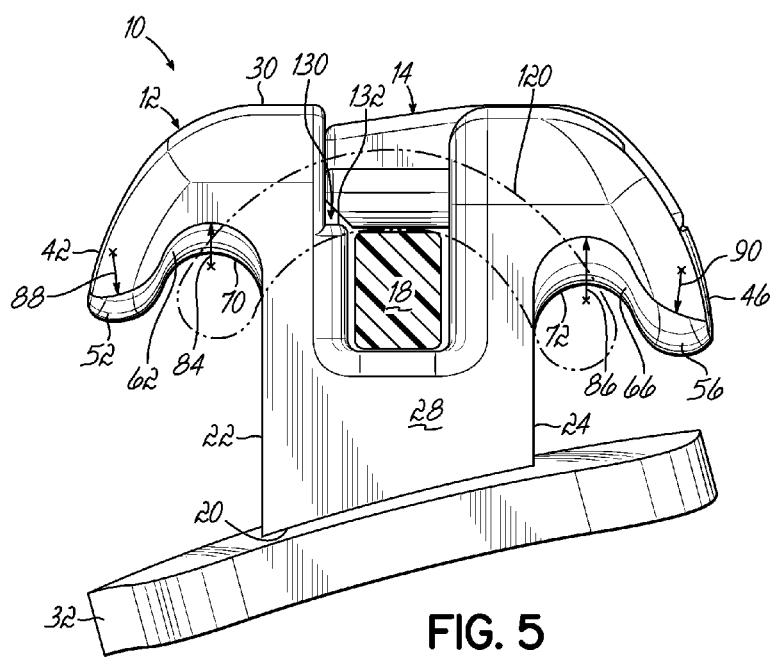
FIG. 5 is a side elevation view of the orthodontic bracket of FIGS. 1 and 2.

As shown in FIG. 5, each of the mid-body regions 70, 72 is continuous with the under tie wing regions 60, 62, 64, 66 such that when viewed from the mesial side 26 and the distal side 28, the under tie wing regions 60, 62, 64, 66 together with the corresponding mid-body regions 70 and 72 have an appearance that is roughly funnel-like in configuration. The under tie wing regions 60, 62, 64, 66 open to one of the mesial side 26 and the distal side 28 over an enlarged area relative to a simple straight projection of the mid-body regions 70, 72 to each of the mesial side 26 and distal side 28. The specific curvatures of the enlarged areas are thought to reduce ligature breakage.

Figure 4:
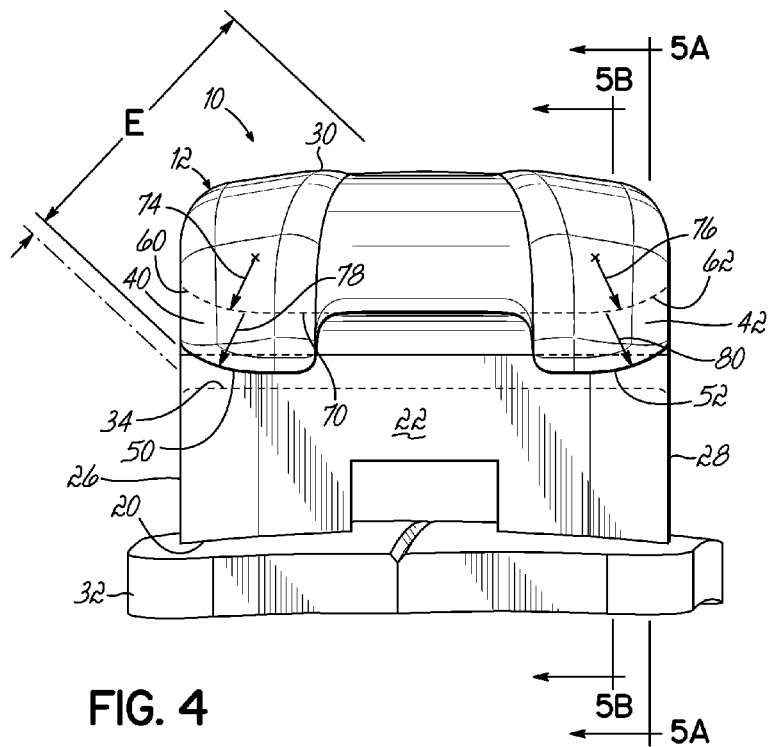
FIG. 4 is a front elevation view of the orthodontic bracket of FIGS. 1 and 2.

Referring now to FIG. 4, each of the tip regions 50 and 52 may form the lingual-most portion of the respective tie wings 40 and 42 and may be rounded in the labial-lingual direction in a plane. That plane may be parallel to the occlusal side 22 and/or one or both of the slot sides 36, 38 of the archwire slot 16. That is, the tip regions 50 and 52 may be curved in the labial direction from the lingual-most portion thereof toward the labial side 30. By contrast, the tips of prior art tie wings are typically straight so as to intersect generally perpendicularly with each side of the bracket.

As shown in FIG. 4, each of the under tie wing regions 60 and 62 may follow a similar curved path (shown in phantom line) relative to the tip regions 50 and 52 and so the under tie wing regions 60 and 62 are curved labially in a region proximate the mesial and distal sides 26 and 28, respectively. The distance over which one or both of the under tie wing regions 60 and 62 and tip regions 50 and 52 are curved may be from one edge of the tie wing 40, 42 to the nearest side 26, 28. In other words, the entire mesial-distal width of the tie wing 40, 42 may be curved in one or both of the under tie wing regions 60 and 62 and tip regions 50 and 52. However, embodiments of the present invention are not limited to a full width curvature, as tie wings having a partial curvature are contemplated. For example, the curvature may extend inwardly from one side 26, 28 to a distance from about 0.010 inch to about 0.050 inch and by way of further example from about 0.010 inches to about 0.030 inch. In this regard, the tie wings 40, 42 may be slightly wider than the curvature over which the under tie wing regions 60 and 62 and tip regions 50 and 52 extend. Although not shown in FIG. 4, each of the under tie wing regions 64 and 66 and the tip regions 54 and 56 of the respective tie wings 44 and 46 may be rounded in the labial-lingual direction in a similar manner as the tie wings 40 and 42.

Further, in one embodiment, the curvature of each of the under tie wing regions 60, 62, 64, 66 and the tip regions 50, 52, 54, 56 may be defined by a radius of curvature and thus lack any edges or discontinuities. With reference to FIG. 4, labial curvature of the tip regions 50, 52 and under tie wing regions 60, 62 may be defined by comparison to the labial-most surface of the mid-body region 70 (shown in phantom line). As shown, the mid-body region 70 extends in a straight line between the tie wing 40 and the tie wing 42 to join with the under tie wing regions 60 and 62 at either end. The straight line of the mid-body region 70 may be parallel to the base surface 34 of the archwire slot 16. The corresponding surfaces of the under tie wing regions 60 and 62 are also shown in phantom line.

As shown, the under tie wing regions 60 and 62 bend labially relative to the corresponding surface of the mid-body region 70. By bending labially, the curvature is toward the labial side 30 at the mesial side 26 for the under tie wing region 60 and is toward the labial side 30 at the distal side 28 for the under tie wing region 62. Relative to the mid-body region 70, as is represented by the phantom line in FIG. 4, the curvature in the under tie wing regions 60 and 62 may be defined by a radius 74 and a radius 76, respectively. The mid-body region 70 represented by the phantom line may be tangent to each of the radii 74, 76 at each end of the mid-body region 70 in embodiments in which the under tie wing regions 60 and 62 extend the full width of the respective tie wings 40, 42. In other embodiments, the mid-body region 70 transitions to a straight portion of the under tie wing regions 60 and 62 which is then tangent to the radii 74, 76. In either embodiment, the radius 74, 76 may be from about 0.010 inch to about 0.050 inch and by way of further example one or both radii 74, 76 may be from about 0.010 inch to about 0.030 inch. Although not shown, the under tie wing regions 64, 66 may have the same or similar curvature in relation to the gingival mid body region 72.

With continued reference to FIG. 4, the tip regions 50 and 52 may each be defined, at least in part, by a radius 78 and a radius 80, respectively, so that the tip regions 50 and 52 are curved in the labial-lingual direction or toward the labial side 30 at their respective sides 26, 28. For example, the radii 78 and 80 may reside in a plane generally parallel with at least one opposed slot surface 36 and/or 38. In one embodiment, the radius 78 and the radius 80 may be the same as the radius 74 and the radius 76, respectively, so that the lingual-most surface of the tip regions 50, 52 are parallel to the labial-most surface of the corresponding under tie wing regions 60, 62.

As is shown in FIG. 4, the tip regions 50, 52 of the tie wings 40, 42 may include a surface that is parallel with the labial-most surface of the mid-body region 70, as indicated by the phantom line, and so a portion of the tip regions 50, 52 is straight with another portion of the tip regions 50, 52 being defined by the corresponding radii 78, 80. Although not shown, the tip regions 54, 56 may have the same or similar curvature in relation to the under tie wing regions 64, 66. That is, the lingual-most surface of the tip regions 54, 56 may be parallel to the labial-most surface of the under tie wing regions 64, 66.

In addition to being curved in the labial-lingual direction, each of the tip regions 50, 52, 54, 56 and the under tie wing regions 60, 62, 64, 66 may be curved in the occlusal-gingival direction or curved in a plane taken generally perpendicular to the longitudinal axis of the archwire slot 16.

Figure 5A:
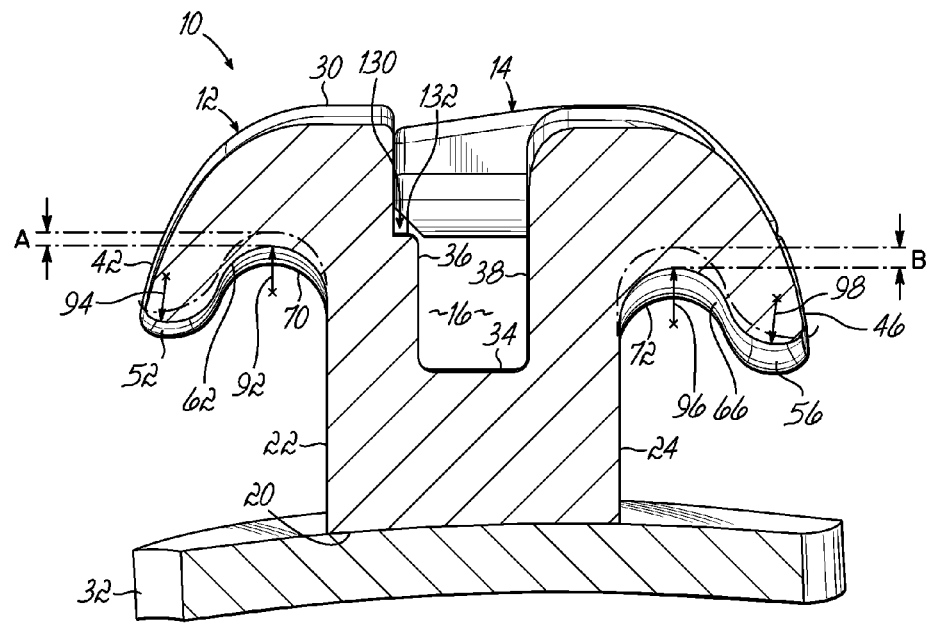
FIG. 5A is a cross-sectional view taken along section line 5A-5A in FIG. 4.
Figure 5B:
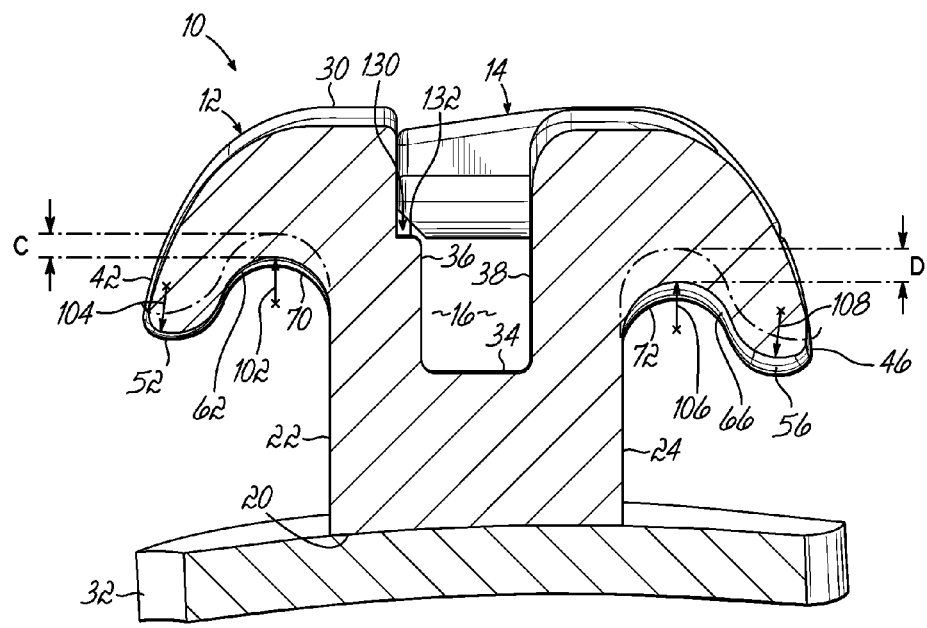
FIG. 5B is a cross-sectional view taken along section line 5B-5B in FIG. 4.

With regard to planes that are generally perpendicular to the longitudinal axis of the archwire slot 16, three planes are shown in FIG. 4 with reference to FIGS. 5, 5A, and 5B. Referring initially to FIG. 5, which depicts the plane of the distal side 28, the tip regions 52, 56 generally have a convex curvature in a plane generally parallel with the distal side 28 whereas the under tie wing regions 62, 66 have a concave curvature in the same plane. This results in an S-shaped curve between the under tie wing regions 62, 66 and the corresponding tip regions 52, 56. The curvatures of each of the regions 52 and 62 and 56 and 66 may mesh together to form a smooth and continuous curvature for each of the tie wings 42 and 46, respectively, for example, in a plane parallel to the distal side 28. Although not shown, the tie wings 40 and 44 may have a similar S-shaped curvature to the tie wings 42 and 46.

In one embodiment, the under tie wing regions 62 and 66 and the tip regions 52 and 56 are defined in part by a corresponding radius of curvature in the plane of the distal side 28 or in close proximity thereto. In particular, and with reference to FIG. 5, the under tie wing region 62 opens to the distal side 28 and may be defined by a radius 84 at the intersection with or in close proximity to the distal side 28. Similarly, the under tie wing region 66 opens to the distal side 28 and may be defined by a radius 86 at the intersection with or in close proximity to the distal side 28. In one embodiment, the radius 84 may be equal to the radius 86, that is, the under tie wing regions 62 and 66 may be similarly curved in relation to the distal side 28. By way of example only, and not limitation, each radii 84 and 86 may be from about 0.005 inch to about 0.020 inch, and by way of further example, each of the radii 84 and 86 may be approximately 0.010 inch.

Each of the tip regions 52 and 56 may also be defined in a similar manner by a radius of curvature. In particular, the tip region 52 may be defined in part by a radius 88 and the tip region 56 may be defined in part by a radius 90. Each of the radii 88 and 90 may lie in the plane of or in close proximity to the distal side 28, as described above with regard to the radii 84 and 86. The transition between the curvature defined by the radius 84 and the curvature defined by the radius 88 may be smooth and continuous. And, the transition between the curvature defined by the radius 86 and the curvature defined by the radius 90 may be smooth and continuous. In this way, the radii 84 and 88 define the curvature of the tie wing 42 at the distal side 28, and the radii 86 and 90 define the curvature of the tie wing 46 at the distal side 28. By way of example only, and not limitation, each of the radii 88 and 90 may be from about 0.005 inch to about 0.030 inch, and by way of further example, each of the radii 84 and 86 may be approximately 0.010 inch. Although not shown, the tip regions 50 and 54 and under tie wing regions 60 and 64 may have the same configuration as one or both of the tip regions 52 and 56 and/or the under tie wing regions 62 and 64.

Referring to FIG. 5A, in one embodiment, at a plane offset from, but generally parallel to, the distal side 28 and within the tie wing 42, the under tie wing region 62 may be defined by a radius 92, and the tip region 52 may be defined by a radius 94. Similarly, in the same plane within the tie wing 46 offset from the distal side 28, the under tie wing region 66 may be defined by a radius 96 and the tip region 56 may be defined by a radius 98. Each of the radii 92, 94, 96, 98 may be offset from the distal side 28 as is indicated by comparison of the section lines of FIG. 4 with FIG. 5A. However, in one embodiment each of the radii 92, 94, 96, 98 are also offset in the lingual direction or toward the lingual side 20 relative to the corresponding radii 84, 86, 88, 90 shown in FIG. 5. This offset is indicated by the distance "A" in FIG. 5A for the tie wing 42, and is indicated by the distance "B" for the tie wing 46. By way of example only, and not limitation, each of the distances A and B may be less than about 0.010 inch and may depend on the radius 76 and/or the radius 80 (in FIG. 4) and similar radii of tie wing 46, and the location of the plane at which the radii are positioned. Although not shown, the tip regions 50, 54 of the tie wings 40, 44 may include similar radii and those radii may be offset in the lingual direction by similar distances as those for the tie wings 42, 46.

In one embodiment, and with reference to the tie wing 42, the radius 88 is equal to the radius 94 and the radius 84 is equal to the radius 92. In this respect, the curvature in the plane of the distal side 28 (FIG. 5) for each of the tip region 52 and the under tie wing region 62 is the same as the curvature in a plane offset from the distal side 28 as indicated in FIG. 5A. In other words, the curvature defined by the radii 84 and 88 at the distal side 28 is the same as the curvature defined by the radii 92 and 94 so that the curvature is constant at and between each plane. Thus the curvature of the tie wing 42 may be achieved by offsetting a single predetermined curvature in the lingual direction according to the radii 76 and 80.

With reference now to FIG. 5B, in a second plane offset toward the mesial side 26 from the plane indicated in FIG. 5A, as is indicated by reference to FIG. 4, the under tie wing region 62 may be defined by a radius 102 and the tip region 52 may be defined by a radius 104. In the same plane within the tie wing 46, the under tie wing region 66 may be defined by a radius 106 and the tip region 56 may be defined by a radius 108. Each of the radii 102, 104, 106, 108 may be offset from the distal side 28. However, in one embodiment, each of the radii 102, 104, 106, 108 are also offset in the lingual direction or toward the lingual side 20 relative to the corresponding radii 92, 94, 96, 98 of FIG. 5A. This lingual offset is indicated by the distance "C" for the tie wing 42, and is indicated by the distance "D" for the tie wing 46 in FIG. 5B. By way of example only, and not limitation, each of the offsets C and D may be less than about 0.010 inch and may depend on the radii that define the labial curvature of the under tie wing regions 62 and 66 in a manner similar to FIG. 4. Although not shown, the tip regions 50, 54 of the tie wings 40, 44 may include similar radii and be offset in the lingual direction by similar distances as the tip regions 54, 56 of the tie wings 42 and 46.

In one embodiment, and with reference to the tie wing 42, the radius 104 is equal to each of the radii 84, 88, 92, 94, 102 and the radius 106 is equal to each of the radii 86, 90, 96, 98, 108. In this respect, the curvature in a given plane for each of the tip region 52 and the under tie wing region 62 and for each of the tip region 56 and under tie wing region 66 is the same as the curvature in another plane offset from the distal side 28. In other words, the curvatures of the tip regions 52, 56 and the under tie wing regions 62, 66 are the same in each plane taken generally perpendicular to the longitudinal axis of the archwire slot 16 but those curvatures are offset in the labial-lingual direction from one plane to the next plane as determined by one or both of the radius 76 and/or the radius 80 and similar radii of tie wing 46. By this configuration, the curvature in each plane of the tip regions 52, 56 and the under tie wing regions 62, 66 is constant with that curvature being offset in the lingual direction from the mesial side 26 or the distal side 28. While only a labial offset in the curvature is shown, it will be appreciated that the curvature may be offset both labially and toward the sidewalls 36, 38 of the archwire slot 16. That is, the curvature may approach the archwire slot 16. So, for example, the curvature of the under tie wing region 62 may be an offset in the labial direction and in the gingival direction and the curvature of the under tie wing region 66 may be an offset in the labial direction and in the occlusal direction.

In one embodiment, the tie wings 40 and 42 may be mirror images of one another and the tie wings 44 and 46 may be mirror images of one another. However, embodiments of the invention are not so limited as each tie wing 40, 42, 44, and 46 may be defined by different radii within the ranges of the radii disclosed herein.

In addition to the curvature, as represented by the S-shaped curves in each of FIGS. 5, 5A, and 5B, the relative positions of the tie wings 40, 42, 44, 46 and the archwire slot 16 are also thought to contribute to a reduction in ligature breakage. As shown in FIG. 5, the labial-lingual positioning of the tie wings 40, 42, 44, 46 relative to the archwire slot 16 also affects the orientation of the ligature 120 as it passes labially over the archwire 18 on each of the mesial side 26 and distal side 28 of the bracket body 12. In particular, the under tie wing regions 60, 62, 64, 66 may be positioned labially of the base surface 34 of the archwire slot 16. This orientation of the under tie wing regions 60, 62, 64, 68 relative to the archwire slot 16 increases the angle between the ligature 120 and the bracket body 12 from about 90° as the ligature 120 exits the under tie wing region and transitions across the sides 26, 28 to ride over the archwire 16. Thus, embodiments of the invention reduce the sharpness of the angle that the ligature 120 bends when installed.

In one embodiment, injection molding may be used to manufacture the bracket body 12 according to embodiments of the invention. As is known in the art, injection molding may include Metal Injection Molding (MIM) in which fine particles of metal and a binder material are mixed together and then injected into a mold cavity. The mold cavity is the shape of the bracket body though larger in size. Once the binder hardens, the molded part, typically called a green body, is removed from the mold. The green body is heated or otherwise treated to remove the binder material, which leaves the metal particles in the form of the bracket body. That object is then sintered (which may include application of pressure) to further improve the strength of the object by increasing density and coalescing the metal particles. Once sintered, the bracket body may be polished to remove any burs. A similar injection molding process is known for ceramic particles and is referred to as Ceramic Injection Molding (CIM).

While it is understood that the curvatures of each of the tie wings 40, 42, 44, 46 and the placement relative to the archwire slot 16, as described above, are thought to reduce ligature breakage, the curves defined by all of the radii must be considered with regard to the strength of the orthodontic bracket. Furthermore, producing the curves was not generally possible without consideration of the strength of the bracket body.

Industry standards may require that the bracket body 12 have a minimum strength to withstand the manufacturing process and/or commercial use without breaking. Consequently, each cross-section of the bracket body 12 may have a minimum thickness requirement such that the bracket body 12 retains at least the minimum strength necessary to withstand orthodontic treatment. For example, each cross-section of the bracket body 12 may be required to have a minimum thickness of between approximately 0.010 inch and approximately 0.015 inch. Therefore, each surface of the under tie wing areas 60, 62, 64, 66 may be spaced from other surfaces of the bracket body 12 to achieve at least the required minimum thickness.

Figure 6:
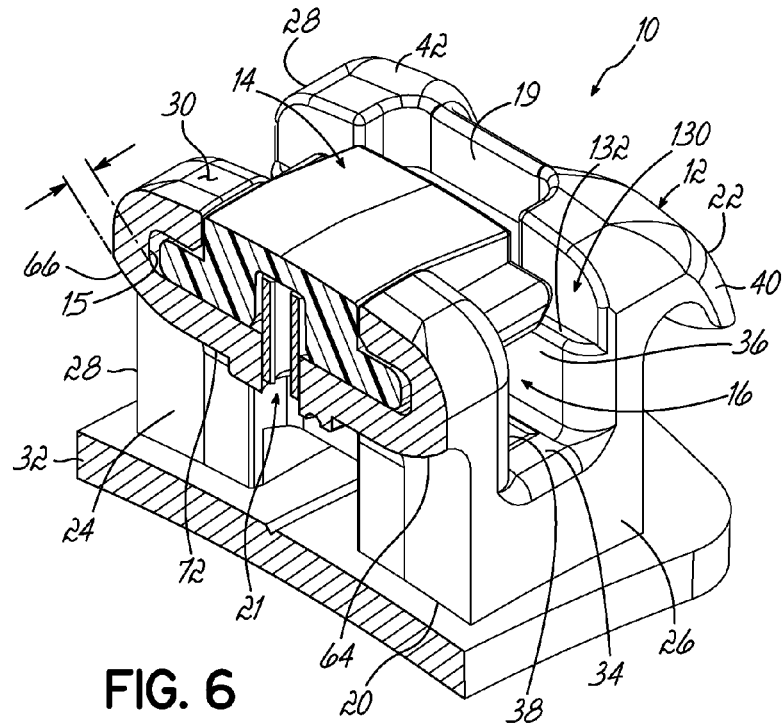
FIG. 6 is a partial cross-sectional view of the orthodontic bracket of FIG. 1 taken along section line 6-6.
Figure 7:
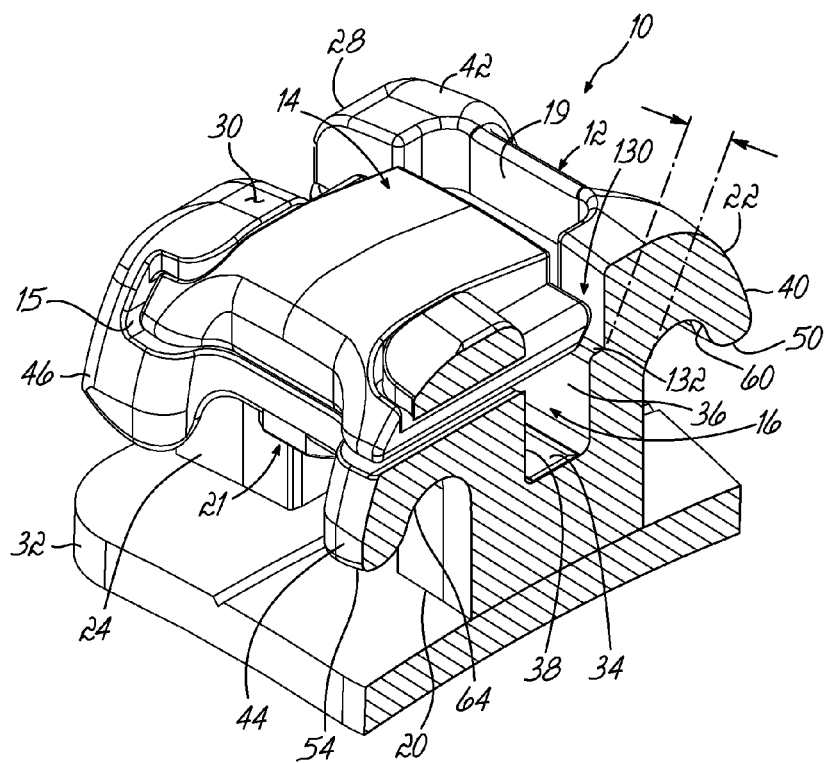
FIG. 7 is a partial cross-sectional view of the orthodontic bracket of FIG. 1 taken along section line 7-7.

Various features of the bracket body 12, such as the tool receptacle 19 and the slide engagement track 15, limit the location and magnitude of curvature, because to achieve the required strength, a minimum thickness must be maintained in each of these areas too. With reference to FIG. 6, the under tie wing regions 64, 66 may be spaced away from the slide engagement track 15 by at least the minimum thickness. Likewise, in another embodiment, the under tie wing regions 60, 62 may be similarly spaced away from the tool receptacle 19. In the exemplary embodiment, and with reference to FIG. 7, a cutout 130 may be formed in the labial side 30 of the bracket body 12 adjacent slot surface 36 that defines a ledge 132 which extends above slot surface 36 and which is configured to engage a lingual side of ligating slide 14 when the ligating slide 14 is in the closed position. The under tie wing regions 60, 62 may be spaced apart from the cutout 130 at a distance of at least 0.010 inch or from about 0.010 inch to about 0.015 inch.

Figure 8A:
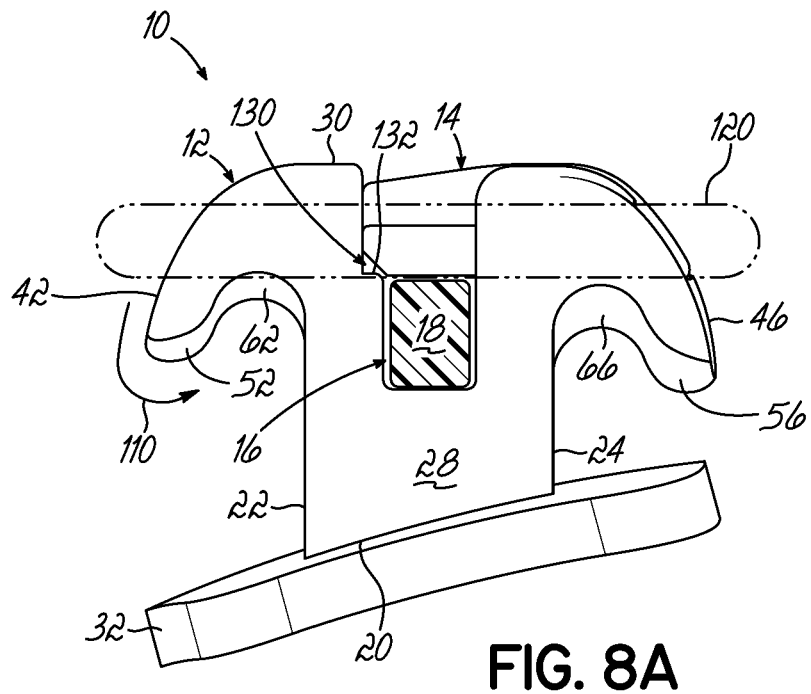
FIGS. 8A-8D are side elevation views of the orthodontic bracket of FIG. 1 illustrating an exemplary installation of a ligature according to one embodiment of the invention.
Figure 8B:
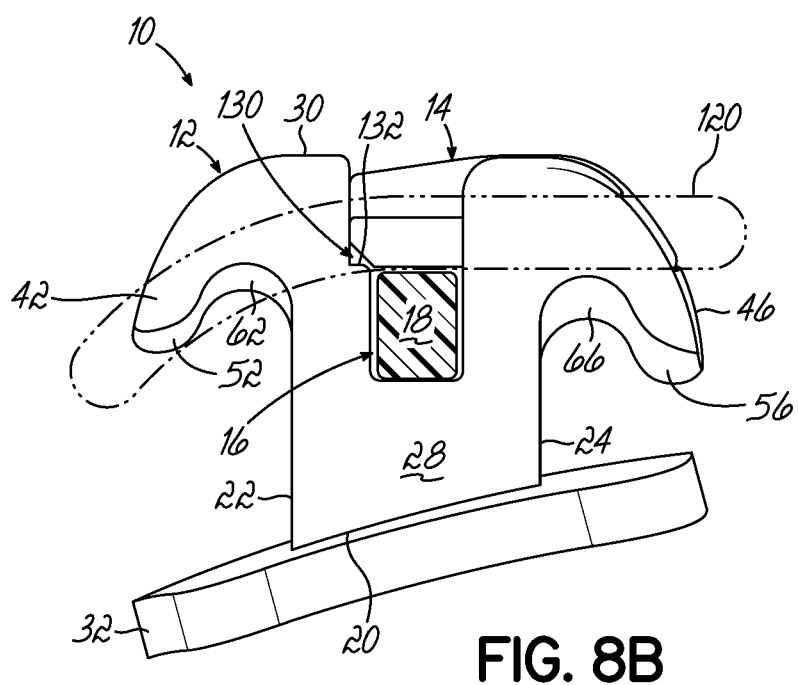
Figure 8C:
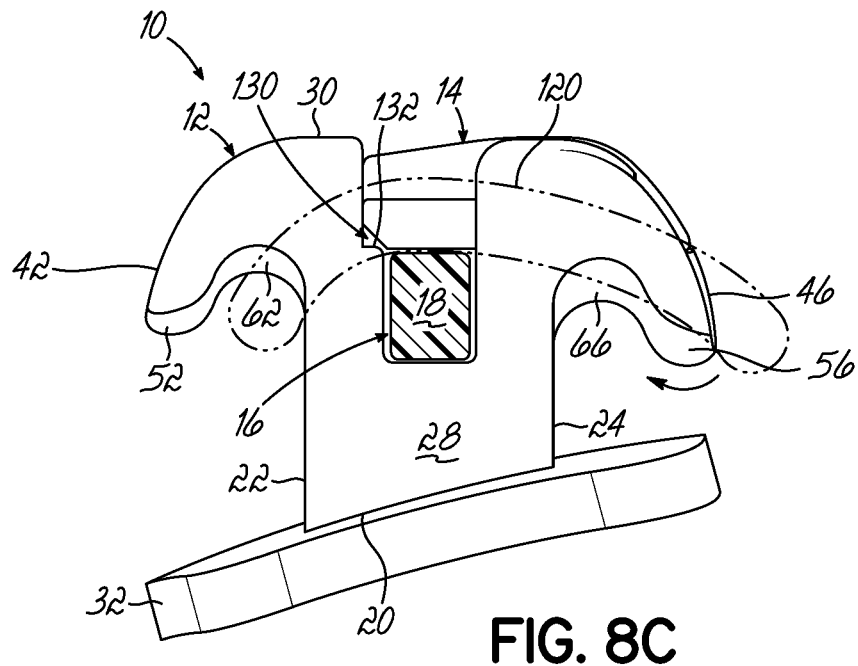
Figure 8D:
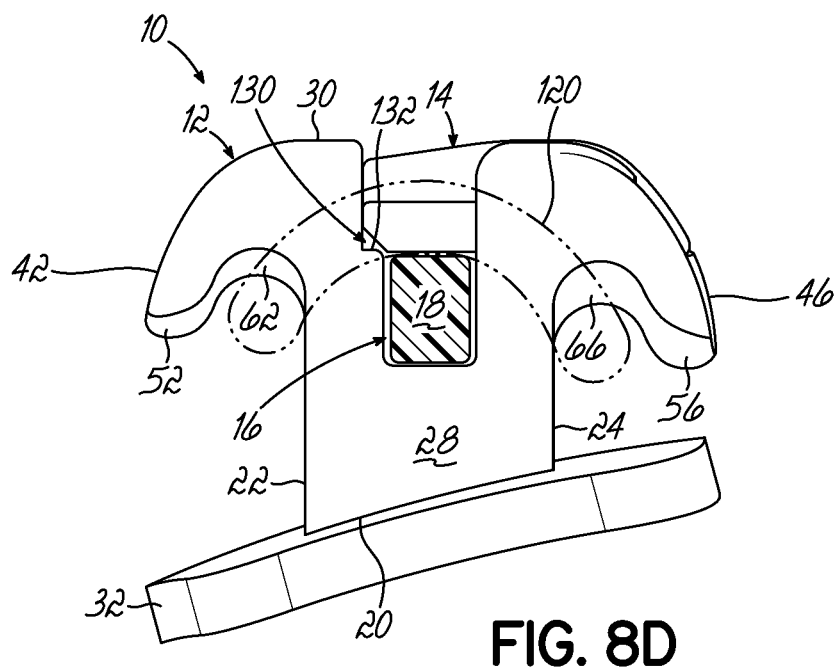

Referring now to FIGS. 8A-8D, the ligature 120 (shown in phantom) may be secured over the bracket body 12 with the archwire 18 positioned in the archwire slot 16. First, a clinician may stretch the ligature 120 and advance it over the tie wing 42 in the direction indicated by arrow 110 (FIG. 8A). Once the ligature 120 has cleared the tip region 52 and with reference to FIG. 8B, the tension of the ligature 120 due to its being stretched may pull the ligature 120 under the second tie wing 42, effectively seating the ligature in place (FIG. 8C). In addition or alternatively, the clinician may push the ligature 120 under the tie wing 42 to seat the ligature 120 in place. This process may then be repeated sequentially for the remaining tie wings such as, for example, the fourth tie wing 46 (FIG. 8C) until installation of the ligature 120 is complete (FIG. 8D).

The labially curved paths of any single one of the tip regions 50, 52, 54, 56 or their combination ease the process of securing the ligature 120 and reduce the risk that the ligature 120 will tear during installation. For example, the curvature of the tip regions 50, 52, 54, 56 minimizes the distance to which the ligature 120 is required to stretch when securing the ligature 120 to the orthodontic bracket 10, and thus makes it easier for the clinician to secure the ligature 120 to the bracket body 12. In turn, this reduces the risk that the ligature 120 will tear during installation. In one embodiment, the curvature of the tip regions 50, 52, 54, 56 may reduce the amount of ligature stretching required by approximately 10%. This stretch distance may be quantified by measuring the distance from the geometric center of the labial side 30 to the intersection of one of the tip regions 50, 52, 54, 56, with the mesial side 26 or the distal side 28, an example measurement of which is shown in FIG. 4 and labeled "E." In terms of actual distances, in one embodiment, the distance between the geometric center of the labial side 30 and the location shown in FIG. 4 may be 0.0709 inch and a comparable distance in accordance with the prior art (shown in phantom line) is 0.0784 inch or a reduction in the distance by 0.0075 inch.

With continued reference to FIGS. 8A-8D, once the ligature 120 is secured, the labially curved paths of the under tie wing regions 62, 66 cause it to extend over the archwire 18 in an arc-like manner, as shown in FIG. 8D. The curved paths of the under tie wing regions 60, 62, 64, 66 relative to the archwire slot 16 provide the ligature 120 with relaxed transition from the under tie wing regions 60, 62, 64, 66 to the mesial side 26 or the distal side 28 of the bracket body 12. In other words, the ligature 120 is not forced to navigate a sharp transition as it leaves the under tie wing regions 60, 62, 64, 66 and rides over the archwire 18. In this manner, the curved paths of the under tie wing regions 60, 62, 64, 66 may also reduce ligature breakage during treatment.

While the installation of the ligature 120 has been described as a sequential, step-by-step process, the clinician may alternatively stretch the ligature 120 over more than one of the tie wings 40, 42, 44, 46, simultaneously and in any combination. For example, the clinician may stretch the ligature 120 over all of the tie wings 40, 42, 44, 46 at the same time. In any event, once installed, the ligature 120 ligates the archwire 18 within the archwire slot 16.

Figure 9:
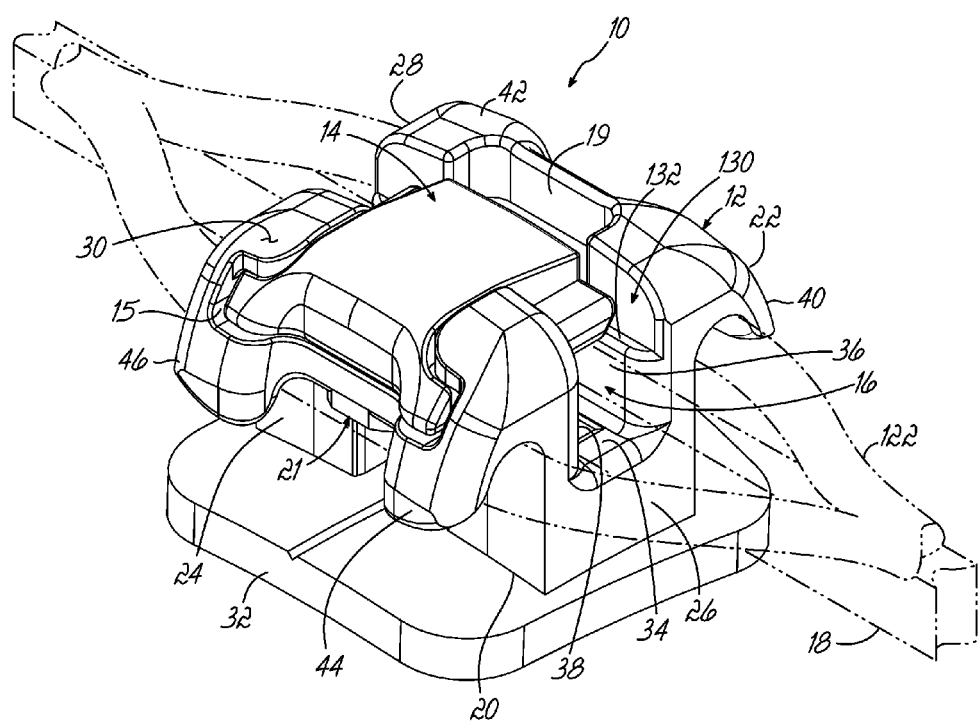
FIG. 9 is a perspective view of the orthodontic bracket of FIG. 1 illustrating a power chain in place of the traditional ligature.

Referring now to FIG. 9, a power chain 122 may be secured to the bracket body 12 in place of the O-ring ligature 120. The curved paths of the tip regions 50, 52, 54, 56 and the under tie wing regions 60, 62, 64, 66 simplify the process of securing the power chain 122 and reduce the risk that the power chain 122 will tear in a manner similar to that described with respect to the ligature 120. In this embodiment, the curved paths of the under tie wing regions 60, 62, 64, 66 may also assist in directing the power chain 122 away from the orthodontic bracket 10 in the mesial-distal direction as the power chain 122 exits the under tie wing regions 60, 62, 64, 66 and moves up over the archwire 18. Specifically, the curved paths of the under tie wing regions 60, 62, 64, 66 may urge the power chain 122 away from the orthodontic bracket 10 labially and over the archwire 18 with a relaxed, reduced angle transition. In this manner, the curved paths of the under tie wing regions 60, 62, 64, 66 may also reduce the risk that the power chain 122 might fail during treatment.

While the present invention has been illustrated by a description of various preferred embodiments and while these embodiments have been described in some detail, it is not the intention of the inventor to restrict or in any way limit the scope of the appended claims to such detail. Additional advantages and modifications will readily appear to those skilled in the art. The various features of the invention may be used alone or in any combinations depending on the needs and preferences of the user.

What is claimed is:

1. An orthodontic bracket for coupling an archwire with a ligature to a tooth, comprising:
    a bracket body configured to be mounted to the tooth, the bracket body including an archwire slot opened to one side of the bracket body and adapted to receive the archwire therein and first and second tie wings extending from the bracket body, the first and second tie wings having first and second tip regions, respectively, and first and second under tie wing regions, respectively, the first and second under tie wing regions configured to receive the ligature,
    wherein the first and second under tie wing regions include first and second curvatures, respectively, the first and second curvatures residing in first and second planes parallel to a longitudinal axis of the archwire slot, respectively, the first and second curvatures extending in the same direction that the archwire slot opens at locations of the first and second curvatures adjacent an outer end of the corresponding under tie wing region,
    wherein the first and second under tie wing regions include third and fourth curvatures, respectively, the third and fourth curvatures being concave and residing in a third plane perpendicular to the longitudinal axis of the archwire slot,
    wherein the first and second under tie wing regions include fifth and sixth curvatures, respectively, the fifth and sixth curvatures being concave and residing in a fourth plane perpendicular to the longitudinal axis of the archwire slot, wherein the fifth curvature is offset from the third curvature in the same direction that the archwire slot opens and the sixth curvature is offset from the fourth curvature in the same direction that the archwire slot opens, and wherein the third and fifth curvatures are each defined by a first radius and the fourth and sixth curvatures are each defined by a second radius, such that the concave curvature is constant between the third and fourth planes.

2. The orthodontic bracket of claim 1, wherein the first and second curvatures are each defined by a radius of at least 0.010 inch.

3. The orthodontic bracket of claim 1, wherein the first and second curvatures are each defined by a radius of at least 0.030 inch.

4. The orthodontic bracket of claim 1, wherein each of the first and second under tie wing regions includes a linearly extending portion.

5. The orthodontic bracket of claim 1, wherein the first and second tip regions include seventh and eighth curvatures, respectively, the seventh and eighth curvatures extending in the same direction as the first and second curvatures, respectively.

6. The orthodontic bracket of claim 1, further including a ligating member movable relative to the archwire slot between an opened position and a closed position.

7. The orthodontic bracket of claim 1, wherein the first and second tip regions include seventh and eighth curvatures, respectively, the seventh and eighth curvatures being convex and residing in the third plane so as to form an S-shaped curve between each under tie wing region and the corresponding tip region in the third plane.

8. The orthodontic bracket of claim 1, wherein the first and second under tie wing regions are each positioned at least partially above a base surface of the archwire slot in the same direction that the archwire slot opens.

9. The orthodontic bracket of claim 1, further comprising third and fourth tie wings, wherein
    the first tie wing extends from an occlusal side of the bracket body adjacent a mesial side of the bracket body, and the third tie wing extends from the occlusal side adjacent a distal side of the bracket body, the second tie wing extends from a gingival side of the bracket body adjacent the mesial side, and the fourth tie wing extends from the gingival side adjacent the distal side, wherein the first under tie wing region is an occlusal under tie wing region extending between the first and third tie wings, and the under second tie wing region is a gingival under tie wing region extending between the second and fourth tie wings,
    wherein the occlusal and gingival under-tie wing regions include the first and second curvatures which each extend in a mesial-distal direction and follow a labially curved path proximate at least one of the mesial or distal side of the bracket body.

10. The orthodontic bracket of claim 5, wherein the seventh and eighth curvatures are each defined by a radius of at least 0.010 inch.

11. The orthodontic bracket of claim 5, wherein the seventh and eighth curvatures are each defined by a radius of at least 0.030 inch.

12. The orthodontic bracket of claim 5, wherein the first and seventh curvatures are each defined by a first radius, and wherein the second and eighth curvatures are each defined by a second radius such that the curvature of each tip region is the same as the curvature of the corresponding under tie wing region.

* * * * *